(12) United States Patent
Spencer et al.

(10) Patent No.: US 10,939,975 B2
(45) Date of Patent: *Mar. 9, 2021

(54) DISPOSABLE GASKET-FILTER ASSEMBLY WITH SEAL INTEGRITY INDICATION FOR STERILIZATION CONTAINER WITH SLIDABLE LOCK HANDLES

(71) Applicant: O & M Halyard, Inc., Mechanicsville, VA (US)

(72) Inventors: Anthony Stephen Spencer, Woodstock, GA (US); Namita A. Mithani, Alpharetta, GA (US); Preston A. Moeller, Alpharetta, GA (US)

(73) Assignee: O&M Halyard, Inc., Mechanicsville, VA (US)

( * ) Notice: Subject to any disclaimer, the term of this patent is extended or adjusted under 35 U.S.C. 154(b) by 77 days.

This patent is subject to a terminal disclaimer.

(21) Appl. No.: 16/293,865

(22) Filed: Mar. 6, 2019

(65) Prior Publication Data
US 2020/0281680 A1 Sep. 10, 2020

(51) Int. Cl.
*A61B 50/30* (2016.01)
*A61L 2/26* (2006.01)
*A61B 50/00* (2016.01)

(52) U.S. Cl.
CPC ............... *A61B 50/30* (2016.02); *A61L 2/26* (2013.01); *A61B 2050/0066* (2016.02); *A61L 2202/24* (2013.01)

(58) Field of Classification Search
CPC .......... A61L 2/26; A61L 2202/24; A61L 2/07; A61L 2202/122; A61L 2/206;
(Continued)

(56) References Cited

U.S. PATENT DOCUMENTS 3,527,400 A 9/1970 Shepherd et al.
3,730,338 A 5/1973 Chesky
(Continued)

FOREIGN PATENT DOCUMENTS

DE 10 2012 102 370 A1 9/2013
WO WO 2008/078169 A2 7/2008
(Continued)

OTHER PUBLICATIONS

AliExpress-Hornet 20 Dram Push Down & Turn Vial Container. AliExpress.com https://www.aliexpress.com/item/33010821944.html?spm=2114.search0302.3.52.6c4f42dfiFT8y2&ws_ab_test=searchweb0_0, searchweb201602_0,searchweb201603_0,ppcSwitch_0& (Year: 2016).*
(Continued)

*Primary Examiner* — Jelitza M Perez
(74) *Attorney, Agent, or Firm* — Dority & Manning, P.A.

(57) ABSTRACT

Sterilization packaging systems with features for sealing a volume against an ingress of contaminants are provided. Such features include a sealing assembly including a gasket and a sheet of filter material. The sealing assembly seals a lid to a seal rim of a base. The gasket has an upper surface, outer edge, and inner edge. The sheet of filter material extends from an inner edge of the gasket, and the gasket completely surrounds the sheet of filter material. The upper surface of the gasket comprises a plurality of indentations that define channels to facilitate delivery of a sterilization agent through the filter material. A sterilization assembly including a lid having a plurality of protrusions in its upper surface and a sliding-lock system for sealing and locking the lid to a container base is also provided.

30 Claims, 13 Drawing Sheets

(58) Field of Classification Search
CPC ...... A61L 2202/182; A61L 2/14; A61L 2/208;
A61L 2/20; A61L 2202/121; A61L 2/022;
A61L 2/00; A61L 9/00; A61L 2/0094;
A61L 2/0017; A61L 2/202; A61L
2202/23; A61L 9/015; A61L 2202/17;
A61L 2202/181; A61B 50/33; A61B
50/30; A61B 50/34; A61B 50/00; A61B
2050/005; A61B 2050/0089; A61B
2090/0814; A61B 90/40; A61B
2017/3466; A61B 2050/0066; A61B
50/20; A61B 50/36; A61B 55/027; B65B
55/04; B65B 31/00; B65B 55/02; B65B
55/12; B01F 15/0206; A61J 1/05; A61J
1/00; A61J 1/1412; A61J 1/18; B01D
2271/02; B65D 51/1616; B65D
2543/00435; B65D 55/02; B65D 81/3216
See application file for complete search history.

(56) References Cited

U.S. PATENT DOCUMENTS

| | | | |
|---|---|---|---|
| 4,193,496 A | 3/1980 | Barratt | |
| 4,349,118 A | 9/1982 | Sanderson et al. | |
| 4,466,552 A | 8/1984 | Butterworth et al. | |
| 4,489,841 A | 12/1984 | Thompson | |
| 4,551,311 A | 11/1985 | Lorenz | |
| 4,643,303 A | 2/1987 | Arp et al. | |
| 4,671,943 A | 6/1987 | Wahlquist | |
| 4,706,839 A | 11/1987 | Spence | |
| 4,774,063 A | 9/1988 | Runnells | |
| 4,919,888 A | 4/1990 | Spence | |
| 5,372,787 A | 12/1994 | Ritter | |
| 5,407,069 A | 4/1995 | Schmieding et al. | |
| 5,573,741 A | 11/1996 | Riley | |
| 5,641,065 A | 6/1997 | Owens et al. | |
| 5,887,745 A | 3/1999 | Wood | |
| 6,099,812 A | 8/2000 | Allen et al. | |
| 6,247,609 B1 | 6/2001 | Gabele et al. | |
| 6,311,838 B1 | 11/2001 | Johnson et al. | |
| 6,350,418 B1 | 2/2002 | Venderpool et al. | |
| 6,589,477 B1 | 7/2003 | Frieze et al. | |
| 6,893,158 B1 | 5/2005 | Tipp et al. | |
| 8,418,872 B2 | 4/2013 | Smith | |
| 8,435,445 B2 | 5/2013 | Kral | |
| 8,623,289 B2 | 1/2014 | Cesa et al. | |
| 8,763,839 B2 | 7/2014 | Sakairi | |
| 8,815,174 B2 | 8/2014 | Bacik et al. | |
| 9,028,147 B2 | 5/2015 | Schmal et al. | |
| 9,125,727 B2 | 9/2015 | Dallafior | |
| 9,610,126 B2 | 4/2017 | Griffin | |
| 10,216,985 B2 | 2/2019 | White et al. | |
| 2003/0080571 A1* | 5/2003 | Schainholz | A61L 2/28 292/310 |
| 2009/0266818 A1 | 10/2009 | Sauvageau | |
| 2010/0154353 A1 | 6/2010 | Cesa et al. | |
| 2012/0260293 A1 | 10/2012 | Young et al. | |
| 2013/0280134 A1* | 10/2013 | Hoffman | A61L 2/26 422/114 |
| 2015/0004076 A1 | 1/2015 | Weisshaupt et al. | |
| 2015/0057945 A1 | 2/2015 | White et al. | |
| 2015/0327934 A1 | 11/2015 | Thomas et al. | |
| 2016/0108566 A1 | 4/2016 | Tseng et al. | |
| 2018/0110554 A1 | 4/2018 | Zarins et al. | |

FOREIGN PATENT DOCUMENTS

WO WO 2016/032853 A1 3/2016
WO WO 2019/006079 A2 1/2019

OTHER PUBLICATIONS

International Search Report and Written Opinion for PCT/US2020/018537, dated Aug. 7, 2020, 15 pages.

* cited by examiner

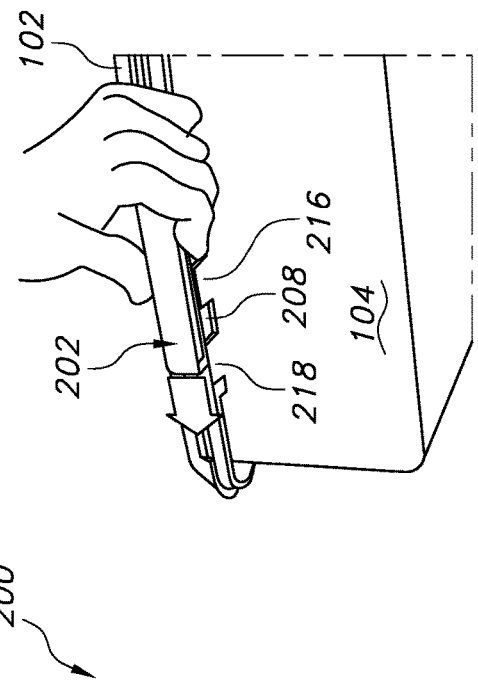
FIG. 12D
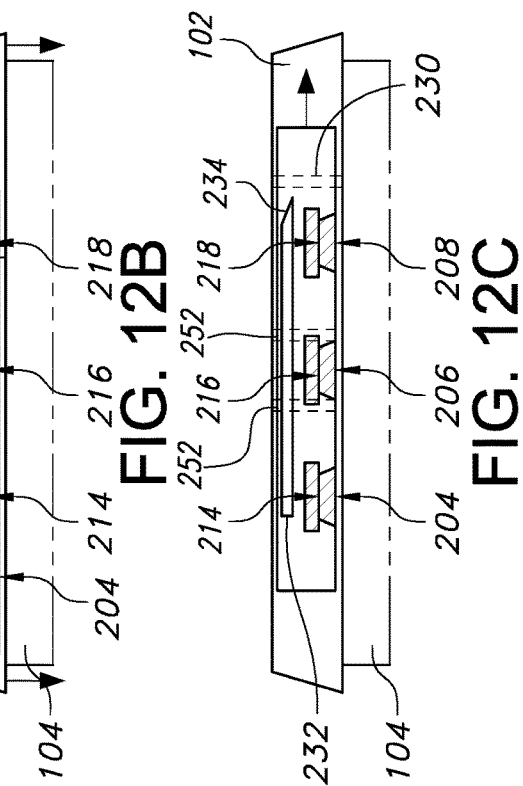
FIG. 12E
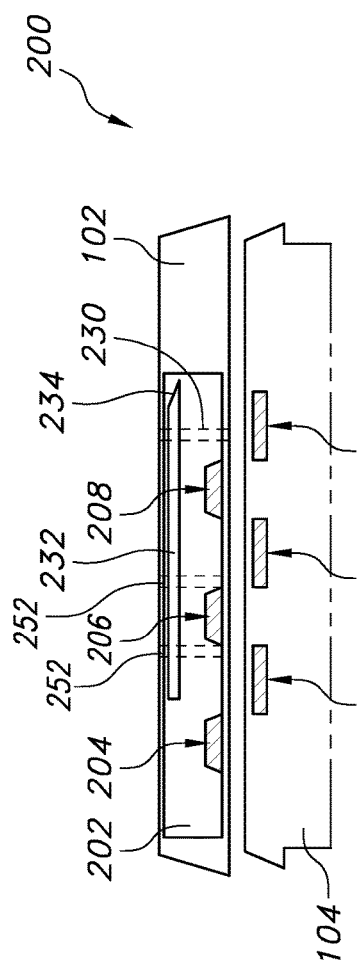
FIG. 12A
FIG. 12B
FIG. 12C

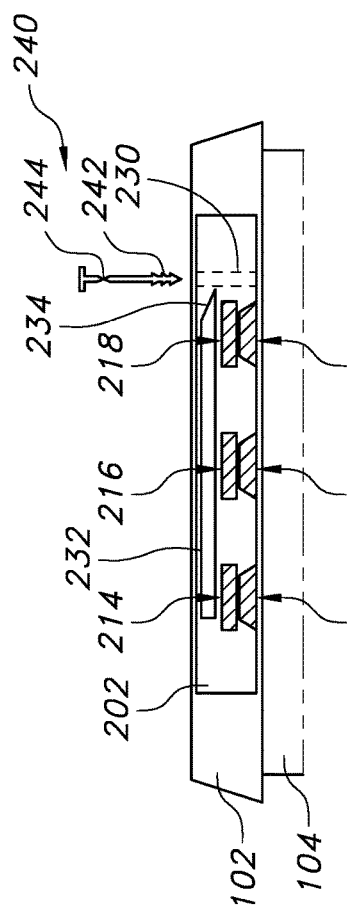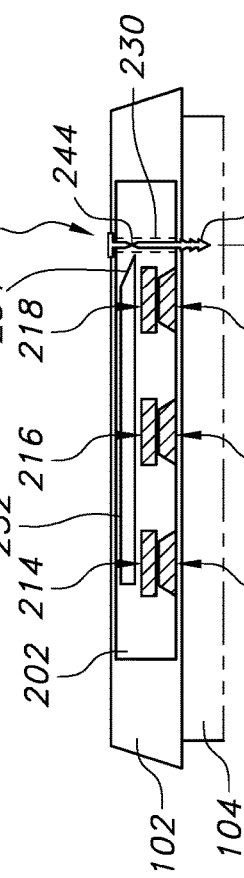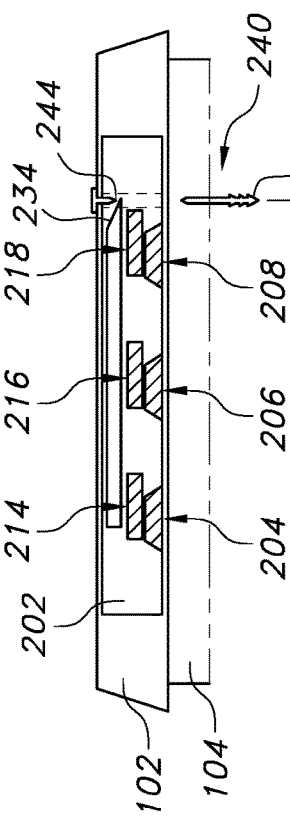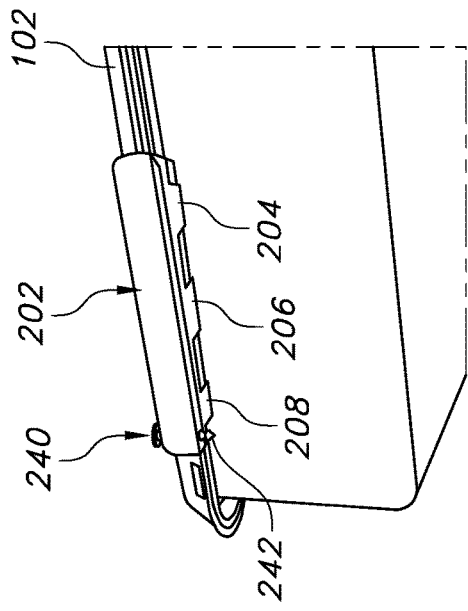

DISPOSABLE GASKET-FILTER ASSEMBLY WITH SEAL INTEGRITY INDICATION FOR STERILIZATION CONTAINER WITH SLIDABLE LOCK HANDLES

FIELD OF THE INVENTION

The subject matter of the present disclosure relates generally to sterilization packaging and sterilization packaging systems.

BACKGROUND

Personnel in the Central Service Room (CSR) or the Sterile Processing Department (SPD) of hospitals are commonly charged with the responsibility of packaging surgical supplies into various types of sterilization packaging systems and sterilizing the systems. The sterilization packaging systems are designed to ensure that the sterility of the packaged contents is maintained from sterilization to the point of reuse. Several activities are involved in the task of preparing and sterilization of medical supplies (e.g., devices, accessories, components, etc.) that are contained in the sterilization packaging system for delivery to the operating room, cardiac catheterization lab, emergency room, labor and delivery room, intensive care unit, pediatric care unit, specialized burn care units, and other surgical or medical units.

Much of the surgical instruments and supplies used in the operating room are reusable. These surgical instruments and supplies typically include such things as: amino hooks, aspirators, hemoclips, bone drills, calipers, footplate impactors, cast cutters, curette, clamps, scalpel blade handles, retractors, forceps, chisels, scissors, clamps, surgeon's towels, basins, custom or specialized surgical instrument sets and the like. All of these supplies must be collected after each procedure, decontaminated, disinfected, washed, dried, sorted and placed in a sterilization packaging system, before sterilization and reused again in another medical procedure. The sterilization packaging systems used must be of the size and shape to accommodate the items to be sterilized, must be compatible with and withstand the physical conditions of the sterilization process, and must be capable of maintaining the sterility of their contents post-sterilization.

Typical means of sterilizing instruments include, among others, autoclaving with pre-vacuum or gravity steam, exposure to ethylene oxide gas, and exposure to hydrogen peroxide plasma or vaporized hydrogen peroxide. After the packaging system and its contents have been sterilized, the sterilization package system typically is allowed to cool and is stored until it is needed for a surgical or medical intervention procedure. When the sterilized packaging system is needed it is transported to the operating room, cardiac catheterization lab, emergency room, labor and delivery room, intensive care unit, pediatric care unit, specialized burn care units, or any other surgical or medical unit.

Common sterilization packaging systems include sealable pouches, sterilization wraps, and rigid containers. Although each of these systems has some advantage compared to other systems, each of these typical packaging systems also has drawbacks. As an example, using a sterilization wrap to package items to be sterilized in a certain prescribed manner will permit the entry of sterilizing vapor/gas or other medium to sterilize the contents of the wrapped package while denying the ingress of contaminants such as bacteria and other infection causing materials or their vehicles after sterilization. As such, sterilization wraps generally provide a consistent barrier against the ingress of contaminants. However, during storage and transfer to the operating room, the wrapped package may be handled several different times; each time the wrapped package is handled, there is a potential that the sterile nature of the package contents can be compromised, e.g., by a tear, cut, or other breach of the wrapping material, which can occur due to over handling or careless manipulation of the wrapped package.

As another example, rigid sterilization containers—such as, e.g., a metallic or polymeric box and a rigid top or lid that closes and seals the metallic or polymeric box—also there is a port (filter or valve) that can permit the entry of sterilizing agent while denying the ingress of contaminants after sterilization. Unlike sterilization wraps, rigid sterilization containers usually avoid tears, cuts, and the like that can compromise the sterilized contents of the container. However, typical rigid sterilization containers are complex packaging systems, including several parts that must be maintained and precisely assembled correctly to prevent compromising the contents of the container after sterilization. Further, some parts of the sterilization container assembly, including the latch member (closure mechanism) which locks the lid to the base container, can be prone to warping, and breakage, as well as dislodgement, and/or other type of cycle related wear damage over the serviceable life of the rigid container. Additionally, the gasketing could experience viscoelastic changes over time due to thermo-mechanical or physical stress associated with repeated sterilization, disinfection, and/or mechanical washing. Thus, even if the parts of the container can be assembled, damaged or worn parts can prevent proper assembly or closure of the sterilization container and thereby increase the potential change for ingress of contaminants after sterilization.

In particular, the gasket that is used to seal the container lid to the container base is typically integrated into the container lid, which is reusable, where such reusability can lead to the formation defects in the gasket. For instance, over time the gasket can experience wear and or tear, which results in a decrease of its compressibility or integrity and, as a result, its sealing performance. Further, deformations in the lid can cause the gasket to be move out of optimal placement with the base, creating a gap in the seal between the lid and the base. In addition, the number of sterilization cycles to which a gasket is subjected is not easily tracked and there is no indication for when a gasket needs to be replaced.

Moreover, considering the filter and gasket design specifically, in some designs, proper filter placement cannot be confirmed once the container is closed. In addition, most rigid containers have complicated assemblies where the filters and gaskets are held in place by retention plates with various locking mechanisms, which complicates the assembly and lead to variation in how a filter is sealed, which increases the risk for bacterial ingress. Furthermore, the gaskets and locking mechanisms for the retention plate can degrade over time, which can also increase the potential for bacterial ingress.

In particular, the locking mechanism that is typically used usually includes a latch mechanism to lock the lid to the bottom or base of the container, often using at least two locks on each container, where each latch has a top latch arm member attached to the lid and a bottom member attached to the base or bottom container. Most commonly, these latches involve a vertical movement in which the latch or handle is transverse in place and then compressed to apply downward tension to lock the latch handle onto the bottom or base of the container. These latch locks may wear over time, and/or the top latch arm may break or become distorted. These issues can result in a reduction in clamping or closing force, which potentially impacts the ability of the sterility of the sterilization container.

Consequently, there is a need for a sterilization packaging system that overcomes the shortcomings of known packaging systems. In particular, a sterilization packaging system that indicates to the user that a proper seal between the lid and base has been achieved would be advantageous. Moreover, a sterilization packaging system that provides a continuous sealing interface, that eliminates the need for retention plates, and that eliminates multiple interfaces associated with the base, lid, gasket, and filter would also be useful. Furthermore, a sterilization packaging system having a locking mechanism that is less prone to breaking or distortion of the locking mechanism and that provides a more uniform seal between the lid and base parts of the containers thereby having improved sealing and more consistent sterility maintenance would also be useful.

SUMMARY

The present invention provides a sealing assembly for a sterilization packaging system. The sealing assembly includes a gasket having an upper surface extending from an outer edge to an inner edge, wherein the upper surface comprises indentations extending from the outer edge to the inner edge, wherein each indentation defines a channel to facilitate delivery of the sterilization agent. The sealing assembly further includes a sheet of filter material extending from an inner edge of the gasket, wherein the inner edge is defined by the first gasket material, wherein the gasket completely surrounds and partially overlaps the sheet of filter material. The gasket facilitates the delivery of sterilization agent through the sheet of filter material when the sterilization packaging system is sealed with the sealing assembly.

In one particular embodiment, the gasket includes a first gasket material and a second gasket material, wherein the first gasket material is less compressible and more rigid than the second gasket material.

In another embodiment, at least one visual indicator can be present on an outer edge of the gasket, wherein the outer edge of the gasket is defined by the first gasket material. Further, a long side of each visual indicator can extend in a vertical direction. Alternatively, a long side of each visual indicator can extend in a direction perpendicular to an upper surface of the sheet of filter material.

In an additional embodiment, the sheet of filter material can extend in a longitudinal direction and a transverse direction, wherein one or more longitudinal support members can be disposed on a surface of the sheet of filter material in the longitudinal direction and one or more transverse support members can be disposed on the surface of the sheet of filter material in the transverse direction.

In a further embodiment, the sealing assembly can provide a continuous sealing interface between a lid and a base of the sterilization packaging system.

In yet another embodiment, the gasket includes a pair of interior facing opposing tabs.

The present invention additionally provides a sterilization packaging system having a volume for containing items to be sterilized. The sterilization packaging system includes a lid having an upper surface defining a perimeter and a lip extending downward from the perimeter, wherein the upper surface comprises a plurality of protrusions, and wherein the lip includes a plurality of openings; and a base having a lower surface, a first sidewall, a second sidewall, a third sidewall, and a fourth sidewall extending from the lower surface, wherein the first sidewall, the second sidewall, the third sidewall, and the fourth sidewall terminate at a seal rim defining a perimeter. The sterilization packaging system also includes a sealing assembly, wherein the sealing assembly seals the lid to the seal rim of the base. The sealing assembly includes a gasket having an upper surface, an outer edge, and an inner edge, wherein the upper surface of the gasket and each of the plurality of protrusions on the upper surface of the lid define a respective channel therebetween, and a sheet of filter material extending from an inner edge of the gasket, wherein the gasket completely surrounds and partially overlaps the sheet of filter material, wherein each channel defined by each of the plurality of protrusions and the upper surface of the gasket facilitates the delivery of sterilization agent through the sheet of filter material when the sterilization packaging system is sealed with the sealing assembly. The sterilization packaging system further includes a sliding-lock mechanism to close and lock the lid to the base, the sliding-lock mechanism comprising a slide-lock handle on the lid, wherein the slide-lock handle comprises a plurality of locking fingers, and wherein the base further includes a plurality of corresponding locking fingers.

In one particular embodiment of the sterilization packaging system, at least one visual indicator is present on the outer edge of the gasket. Further, the visual indicator can be visible from an opening in the lip when the sterilization packaging system is adequately sealed by the sealing assembly. Moreover, the visual indicator can protrude from an opening in the lip when the sterilization packaging system is adequately sealed by the sealing assembly.

Additionally, the plurality of openings on the lip of the lid can include horizontal openings, vertical openings, or a combination thereof. Moreover, horizontal openings can align with each of the plurality of protrusions to facilitate delivery of the sterilization agent through the sheet of filter material via the channels when the sterilization packaging system is sealed with the sealing assembly. Further, the plurality of openings can include the horizontal openings and the vertical openings that are alternately disposed around the lip of the lid. Alternatively, the at least one visual indicator can be visible from at least one respective vertical opening when the sterilization packaging system is adequately sealed by the sealing assembly. Additionally, the at least one visual indicator can protrude from at least one respective vertical opening when the sterilization packaging system is adequately sealed by the sealing assembly.

In another embodiment, the openings on the lip of the lid can include upper openings and lower openings. Further, the upper openings can align with each of the plurality of protrusions to facilitate delivery of the sterilization agent through the sheet of filter material via the channels when the sterilization packaging system is sealed with the sealing assembly. Moreover, the at least one visual indicator can be visible from a respective one of the lower openings when the sterilization packaging system is adequately sealed by the sealing assembly. Further, the at least one visual indicator can protrude from a respective one of the lower openings when the sterilization packaging system is adequately sealed by the sealing assembly.

In yet another embodiment of the sterilization packaging system, the gasket can include a first gasket material and a second gasket material, wherein the first gasket material is less compressible and more rigid than the second gasket material. Further, the inner edge of the gasket can be defined by the first gasket material.

In still another embodiment, the sheet of filter material can extend in a longitudinal direction and a transverse direction, wherein one or more longitudinal support members is disposed on a surface of the sheet of filter material in the longitudinal direction and one or more transverse support members is disposed on the surface of the sheet of filter material in the transverse direction.

In one more embodiment, the sealing assembly can provide a continuous sealing interface between the lid and the base of the sterilization packaging system.

In a further embodiment, the gasket can include a pair of interior facing opposing tabs.

In an additional embodiment, the plurality of protrusions can extend an overhang distance past an inner edge of the upper surface of the gasket to ensure the sterilization agent can reach the sheet of filter material.

In one more embodiment the upper surface of the gasket can include a plurality of indentations and protrusions, wherein each of the plurality of indentations aligns with the protrusions on the lid to define each respective channel.

The present invention further provides a sliding-lock system for closing and locking together a base and a lid of a container, the base having a lower surface, a first sidewall, a second sidewall, a third sidewall, and a fourth sidewall extending from the lower surface, wherein the first sidewall, the second sidewall, the third sidewall, and the fourth sidewall terminate at a seal rim defining a perimeter, the lid having an upper surface defining a perimeter corresponding to the perimeter of the base and a lip extending downward from the perimeter. The sliding-lock system includes a plurality of locking fingers protruding from the seal rim of at least one sidewall of the base; a slide mount positioned above the plurality of locking fingers on the base; and at least one handle, wherein each handle is positioned on the lip of the lid, further wherein each handle has a plurality of locking fingers corresponding to the locking fingers of the base. When the lid is pushed down on the base, the locking fingers of the base engage the locking corresponding fingers of the lid, such that the handle slides horizontally in a locking direction guided by the slide mount to tighten and lock the lid in place on the base.

In one particular embodiment of the sliding-lock system, the handle further can include an aperture for inserting a tamper-proof tag when the lid is locked in place on the base.

In another embodiment, the sliding-lock system further can include a tamper proof tag inserted through the aperture, further wherein the tamper-proof tag may be cut by a cutting edge of the slide mount when the handle is slid in a direction opposite the locking direction.

In an additional embodiment, the locking fingers of the base can be disposed vertically above the corresponding locking fingers of the lid when the lid is locked in place on the base.

In a further embodiment, the plurality of locking fingers of the base each can have a rectangular cross-sectional shape.

In still another embodiment, each of the plurality of locking fingers of the at least one handle can have opposing angled sliding side surfaces for sliding along the locking fingers of the base.

In one more embodiment, each of the plurality of locking fingers of the at least one handle can have a trapezoidal cross-sectional shape.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which:

FIGS. 12A-C provide a cross-sectional illustration of the locking mechanism according to an exemplary embodiment of the present invention.

FIG. 12D provides a perspective view of the locking mechanism according to FIGS. 12A-C.

FIG. 12E provides a perspective view of the ball plunger of the locking mechanism of FIGS. 12A-C.

FIGS. 13A-C provide a cross-sectional illustration of the locking mechanism according to an exemplary embodiment of the present invention having a tamper-proof tag in various stages of operation.

FIG. 13D provides a perspective view of the locking mechanism with a tamper-proof tag according to FIGS. 13A-C while in use.

DETAILED DESCRIPTION

Figure 1:
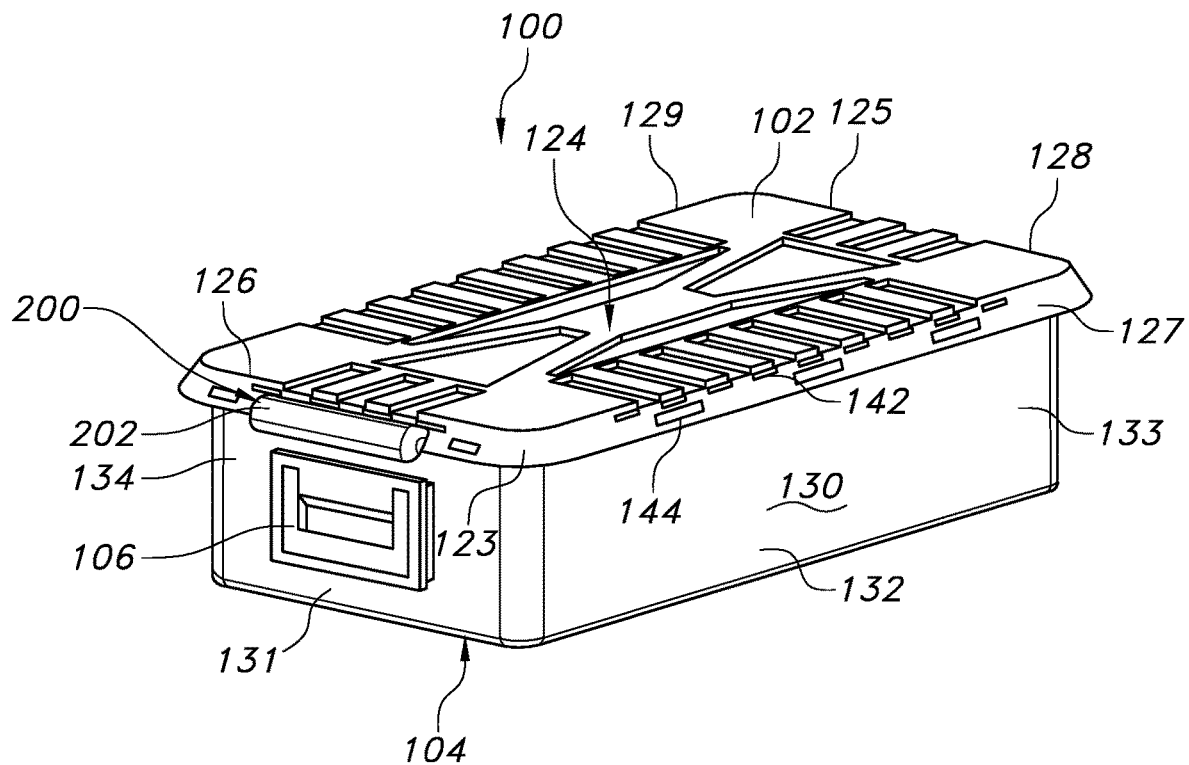
FIG. 1 provides a perspective view of a sterilization packaging system according to an exemplary embodiment of the present invention.
Figure 2:
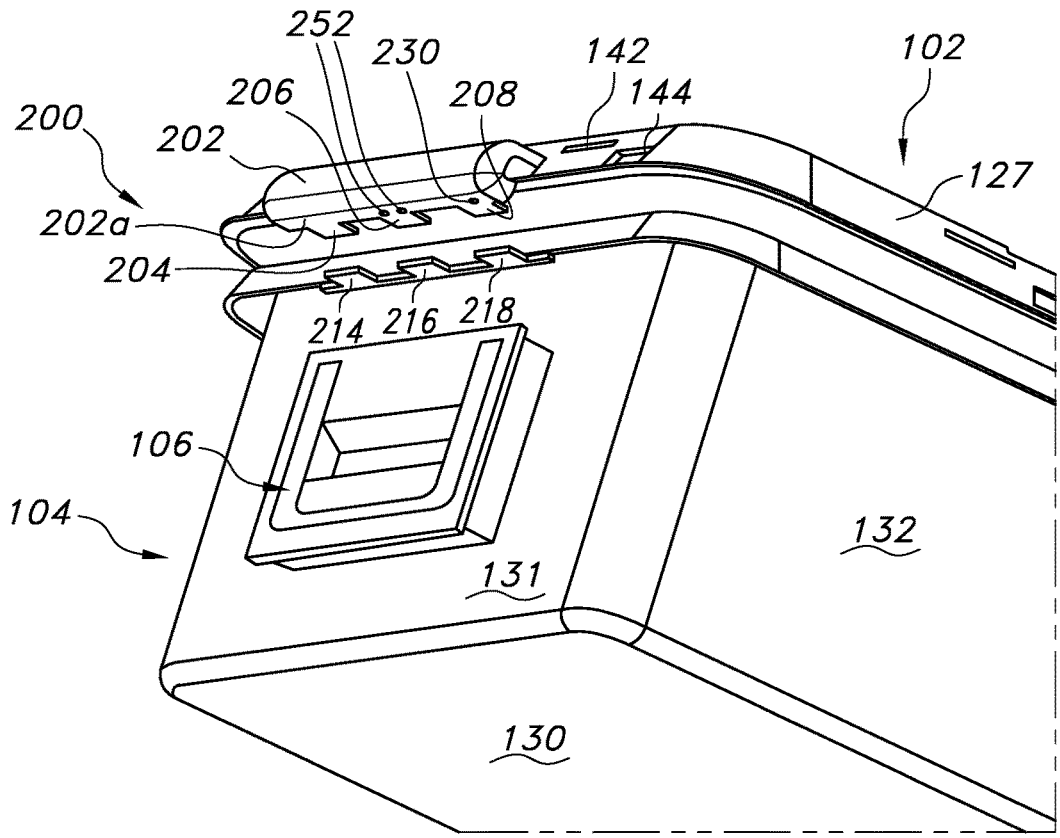
FIG. 2 provides a perspective view of a sterilization packaging system having a locking mechanism according to an exemplary embodiment of the present invention.

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment.

Thus, it is intended that the present invention covers such modifications and variations as come within the scope of the appended claims and their equivalents.

As used herein, the terms "about," "approximately," or "generally," when used to modify a value, indicates that the value can be raised or lowered by 5% and remain within the disclosed embodiment.

Described herein is a sterilization packaging system and components thereof suitable for use in a variety of sterilization modalities and for containing, sterilizing, storing, and aseptic presentation of sterilized items such as surgical instrument and medical supplies. While described in conjunction with its use in hospital and surgical room procedures, the present subject matter is intended for use wherever there is a need for sterilized surgical instrument, medical materials or the like. Consequently, the following description should not be considered a limitation as to the scope of use of the present subject matter.

Generally speaking, the present invention is directed to sterilization packaging systems with features for sealing a volume against an ingress of contaminants. Such features include a sealing assembly that includes a gasket and a sheet of filter material, where the sealing assembly seals a lid to a seal rim of a base. The gasket has an upper surface, an outer edge, and an inner edge, wherein the upper surface of the gasket comprises indentations (or shape profile) extending from the outer edge to the inner edge, and an upper surface of the lid includes a plurality of protrusions, wherein a plurality of channels are respectively defined between each of the plurality of protrusions and the upper surface of the gasket. The sheet of filter material extends from an inner edge of the gasket, where the gasket completely surrounds and at least partially overlaps or encases the sheet of filter material or medium. For example, the gasket can completely encase a perimeter of the sheet of filter material or medium. Further, each channel defined by the upper surface of the gasket and each of the plurality of protrusions facilitates the delivery of sterilization agent through the sheet of filter material when the sterilization packaging system is sealed with the sealing assembly. The sterilization packaging system provides additional features for sealing the volume against an ingress of contaminants such as a locking mechanism for closing and locking a lid to a base of the sterilization packaging system with the sealing assembly disposed between the lid and the base. The locking mechanism may include a sliding-lock system having a plurality of locking fingers on the base and on a slide-lock handle on the lid, respectively. The slide-lock handle slides in a horizontal locking direction, guided by a slide mount on the base, to tighten and lock the lid in place on the base. Further, the sliding-lock system may include a tamper-proof tag to indicate when the packaging system has been opened and the seal has been broken post sterilization.

Figure 6:
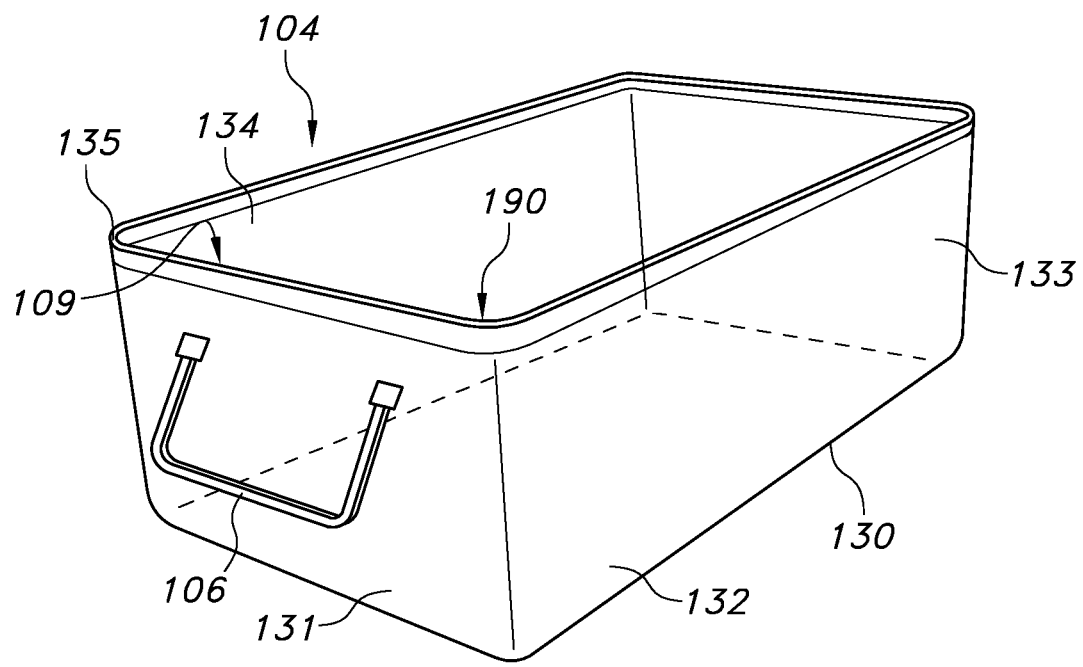
FIG. 6 provides a perspective view of the base of the sterilization packaging system of FIG. 1 according to an exemplary embodiment of the present invention.
Figure 7:
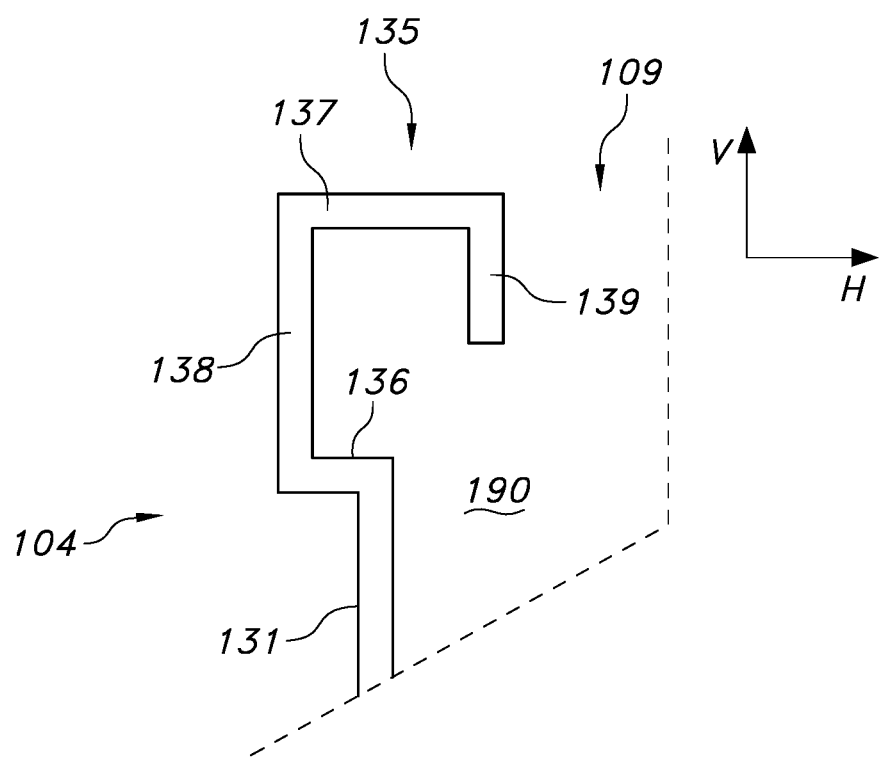
FIG. 7 provides a partial cross-section view of the base of the sterilization packaging system of FIG. 6.
Figure 8:
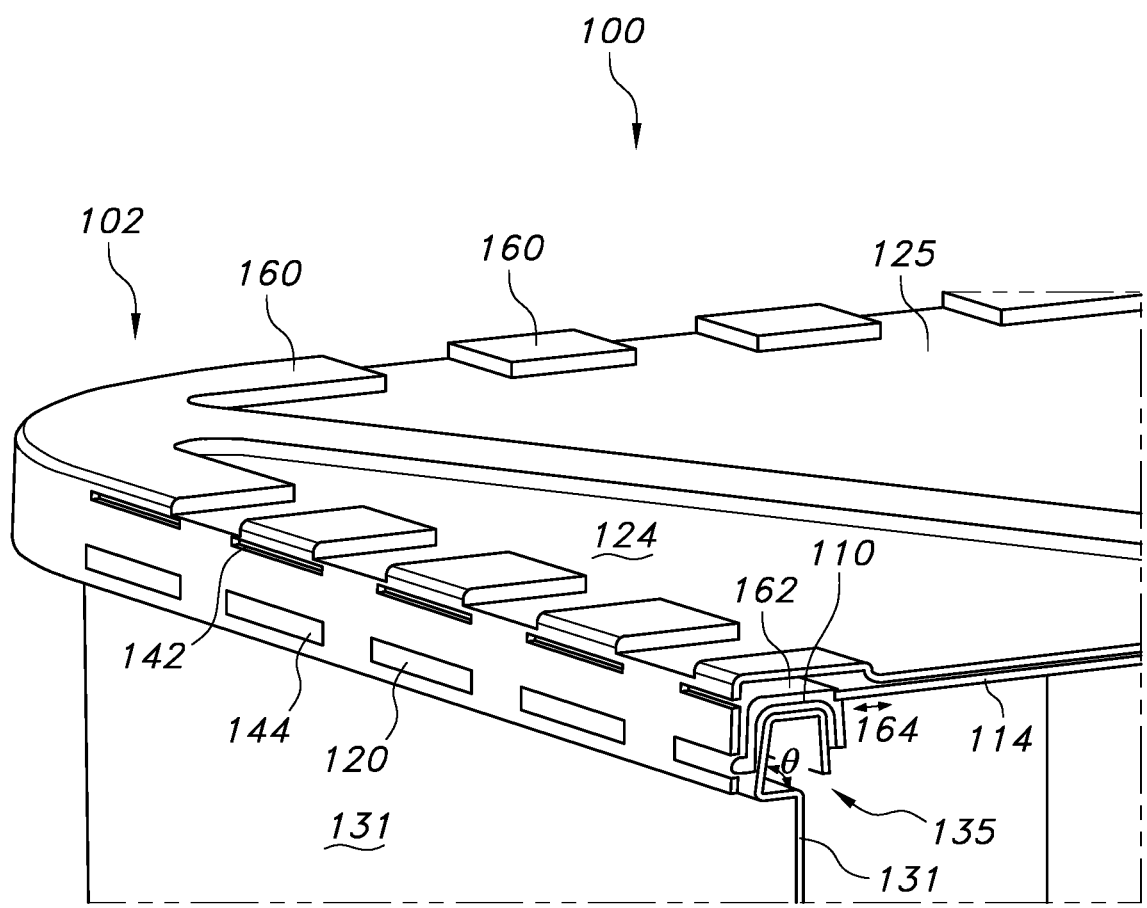
FIG. 8 provides a partial perspective view of the sterilization packaging system when properly sealed by the sealing assembly according to an exemplary embodiment of the present invention.
Figure 9:
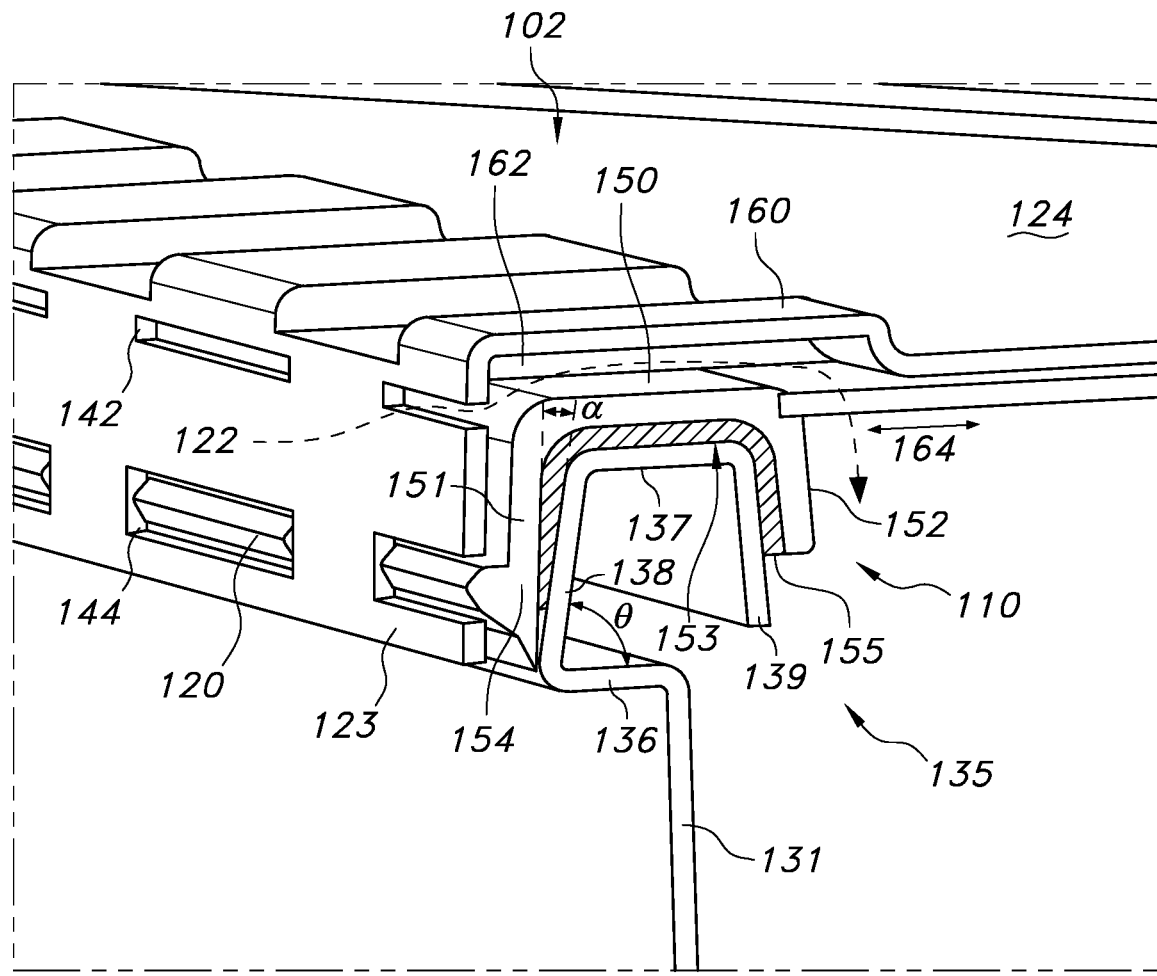
FIG. 9 provides another partial perspective view of the sterilization packaging system of FIG. 8.

Specifically, FIG. 1 provides a perspective view of a sterilization packaging system according to an exemplary embodiment of the present subject matter. In the depicted embodiment, sterilization packaging system 100 includes a lid 102 and a base 104 defining a volume 190 (see FIG. 6) for containing one or more items to be sterilized. The base 104 includes a lower surface 130, a first sidewall 131, a second sidewall 132, a third sidewall 133, and a fourth side wall 134 extending from the lower surface 130, where one or more handles 106 can be present on one or more of the sidewalls, although FIG. 1 shows a handle 106 present on the first sidewall 131. Referring to FIG. 6, which shows the base 104 without the lid 102 attached thereto, the first sidewall 131, the second sidewall 132, the third sidewall 133, and the fourth side wall 134 terminate at a seal rim 135. The various features of the seal rim 135 and how the seal rim 135 cooperates with the lid 102 to create a seal are shown in FIGS. 7-9 and are discussed in more detail below. The base 104 also includes an opening 109 to provide access to the volume 190 in which items to be sterilized can be placed.

Figure 10:
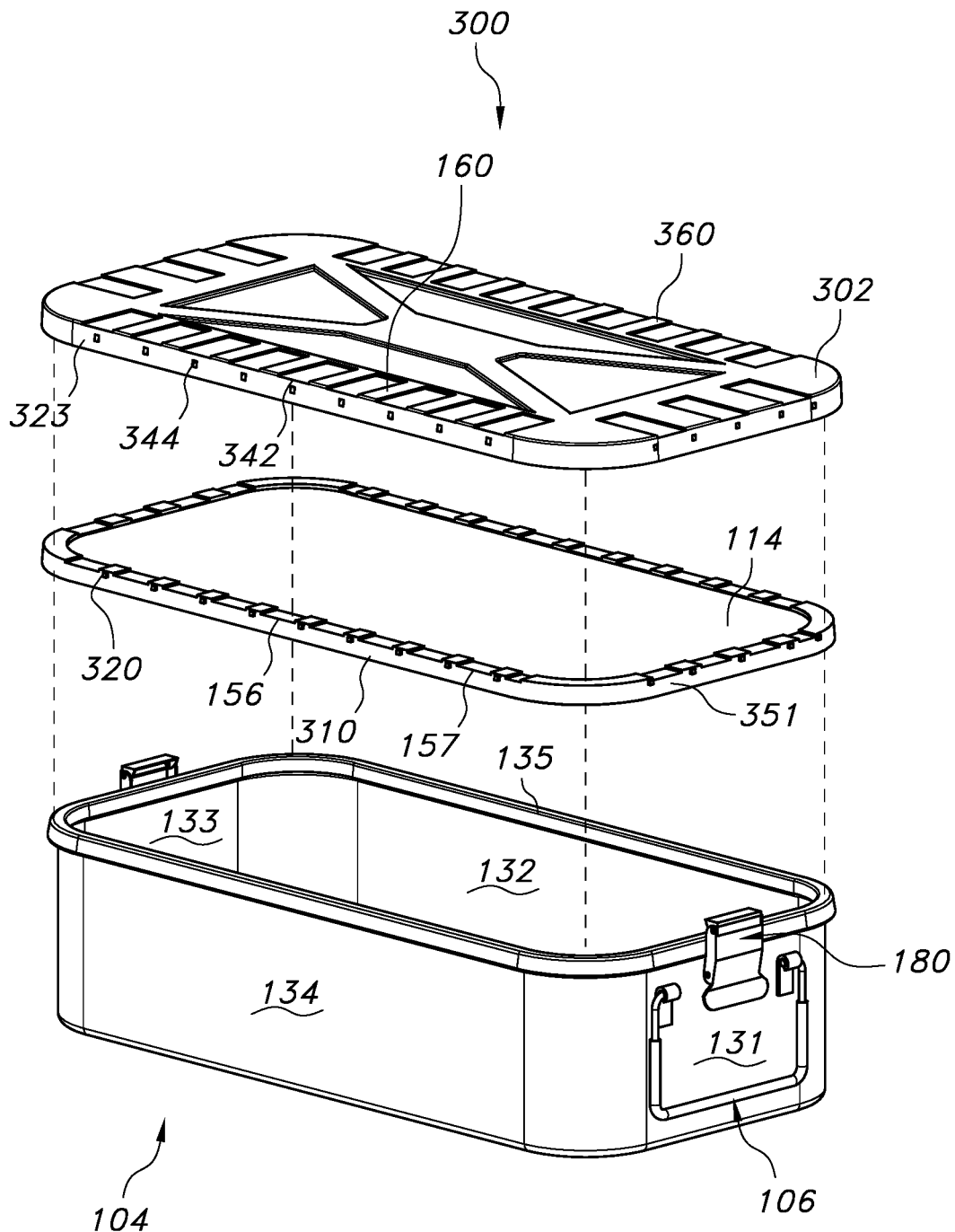
FIG. 10 provides an exploded view of a sterilization packaging system according to another exemplary embodiment of the present invention.

Referring again to FIG. 1, the lid 102 includes an upper surface 124 defining a perimeter 125, where a lip 123 extends downward therefrom towards the base 104. The lip 123 includes a plurality of upper openings 142 and a plurality of lower openings 144 that can be positioned along a first side 126, a second side 127, a third side 128, and a fourth side 129 of the lip 123. The upper openings 142 facilitate the introduction of any suitable type of sterilization agent (e.g., steam, ethylene oxide, or hydrogen peroxide plasma/vaporized hydrogen peroxide) into the opening 109 in the base 104 as discussed in more detail below with respect to FIGS. 8 and 9. Meanwhile, the lower openings 144 can expose a visual indicator 120 when the lid 102 is adequately and properly sealed to the base 104 via a sliding-lock system 202 that serves to engage and compress a sealing assembly between the lid 102 and the base 104. Alternatively, as shown in FIG. 10, the lid 102 may be sealed to the base 104 via a conventional vertical-swinging latch 180. The base 104 and the lid 102 can be reusable and can be formed from a rigid and durable material such stainless steel, anodized or non-anodized aluminum, polyetheretherketone (PEEK), polyaryletherketone, polyphenylsulphone (PPSU), polysulphone (PSU), filled PPSU, and filled PSU. Once sealed, the sealed sterilization packaging system 100 can then be transferred to sterilizing equipment and exposed to sterilization conditions as generally known in the art. Such sterilization conditions can include, for example, steam, ethylene oxide, or hydrogen peroxide plasma/vaporized hydrogen peroxide sterilization conditions. Sterilization conditions are the conditions present during a particular sterilization methodology utilized that substantially kills or completely destroys bacteria and other infectious organisms in or on an industrial or medical device, component or accessory to the desirable sterility assurance level (e.g., 12-log reduction with the overkill method of validation, because it achieves an SAL of 10-6, which means there is a one in a million chance of retaining any trace of surviving microbes for terminal sterilization).

Figure 3:
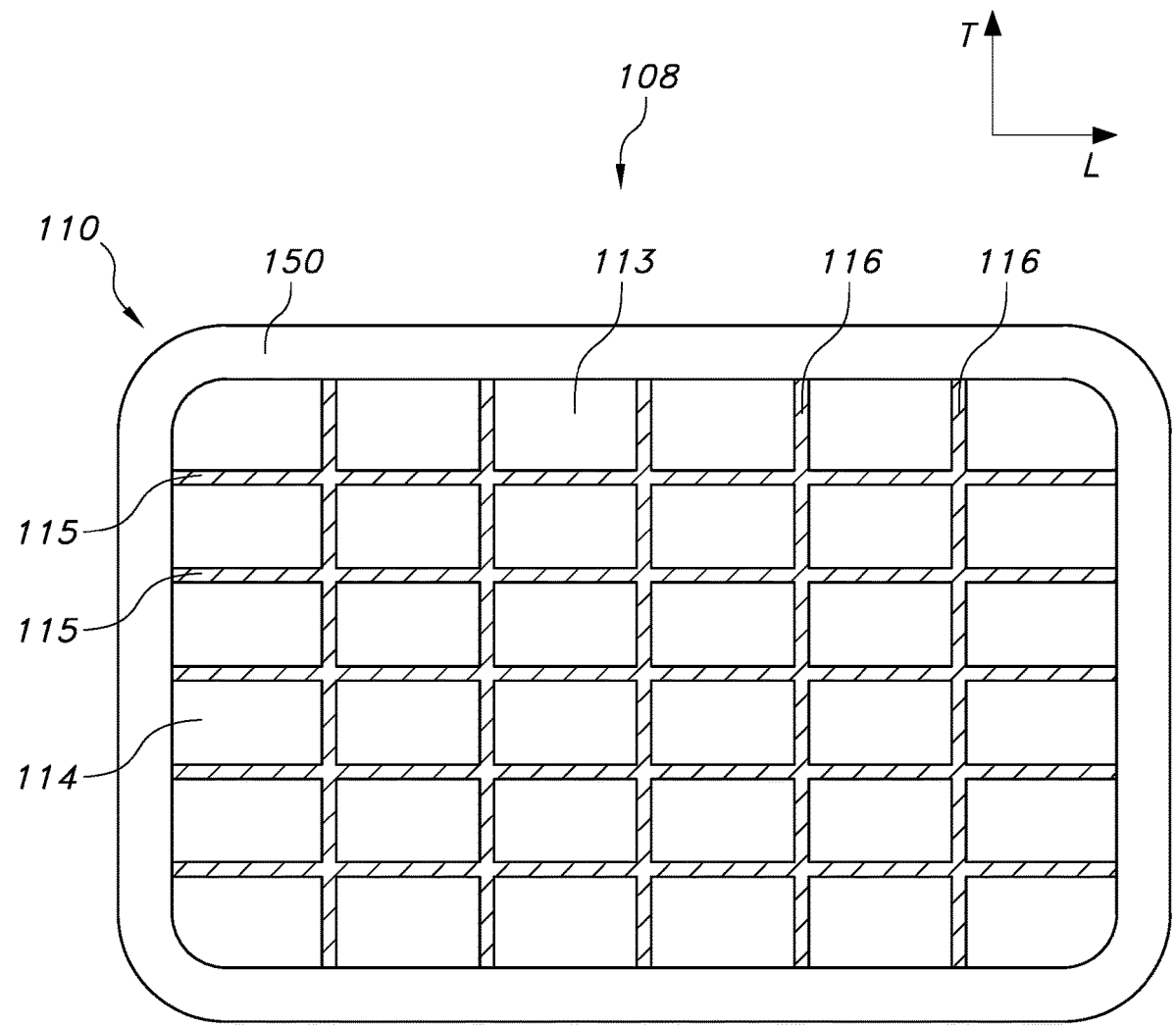
FIG. 3 provides a top view of a sealing assembly, including a gasket and a filter, utilized in the sterilization packaging system of FIG. 1 according to an exemplary embodiment of the present invention.
Figure 4:
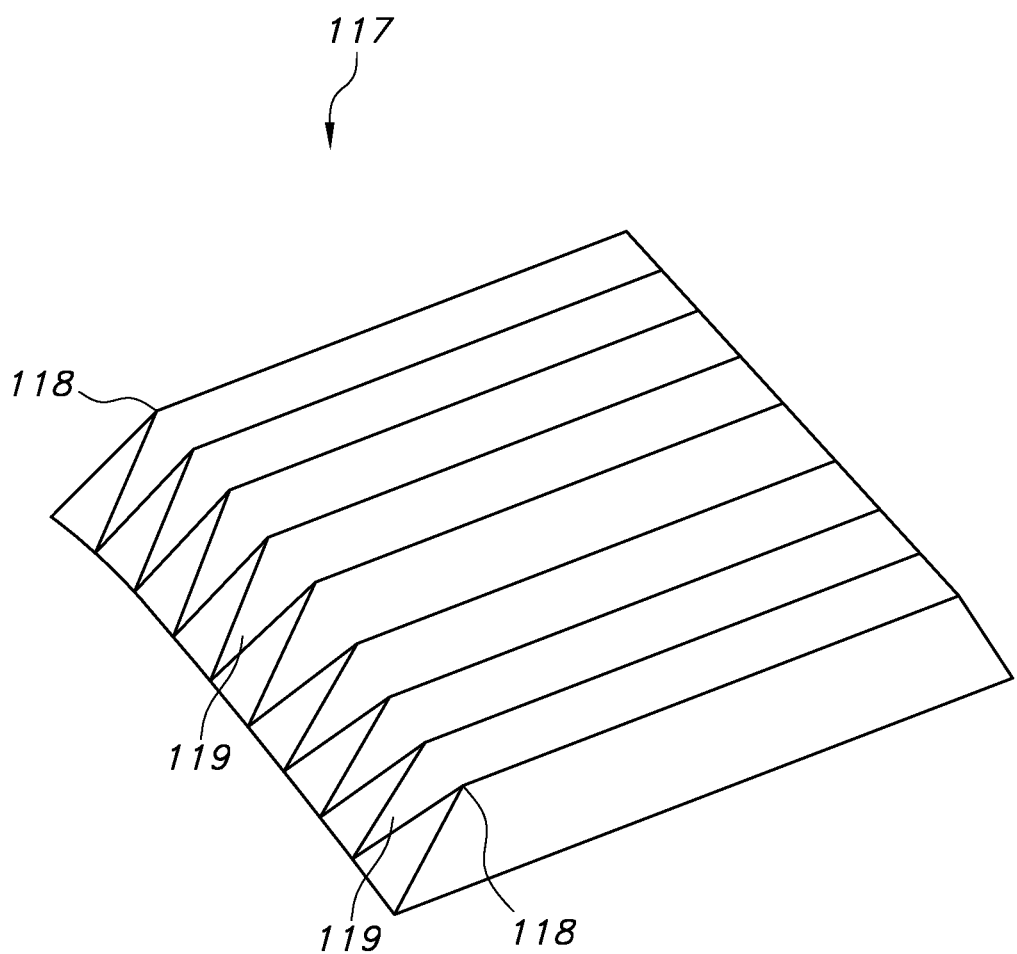
FIG. 4 provides a perspective view of a sheet of filter material utilized in the sealing assembly of FIG. 3 according to an exemplary embodiment of the present invention.
Figure 5:
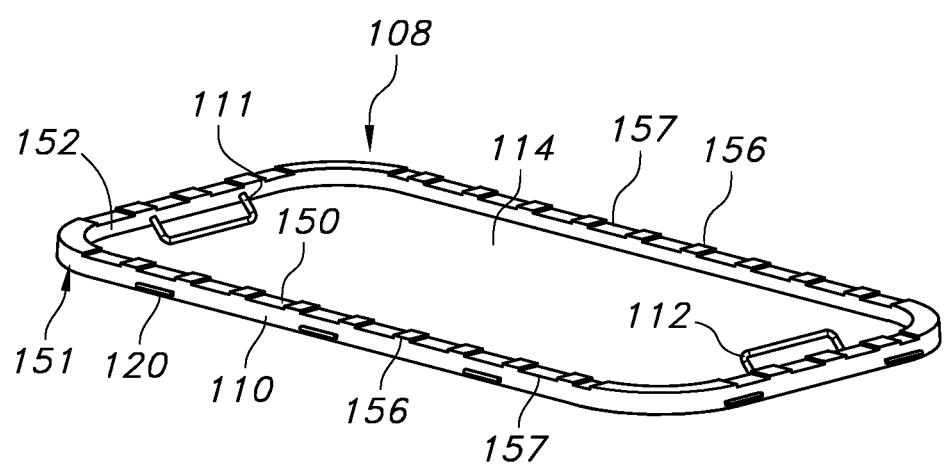
FIG. 5 provides a top view of a gasket utilized in the sterilization packaging system of FIG. 1 according to an exemplary embodiment of the present invention.

Specifically, referring now to FIGS. 3 through 5, the lid 102 is sealed to the base 104 via a one-piece sealing assembly 108 that is engaged and compressed via sliding-lock system 200 (see FIG. 1) or vertical latch 180 (see FIG. 10). The sealing assembly 108 can be disposable or reusable and can seal the base 104 from the ingress of contaminants such as, e.g., bacteria and other infection causing materials or their vehicles. As shown in FIG. 3, the sealing assembly 108 can include a gasket 110 and a sheet of filter material or media 114. The gasket 110 completely surrounds and cases the sheet of filter material or media 114.

The sheet of filter material media 114 can be made from a number of materials and, generally, may be disposable in that the sheet of filter material 114 can be a one-use item that is discarded or recycled after their initial use. Generally, disposable materials can include nonwoven materials made from either or both natural and synthetic fibers such as paper, fibrous polymeric nonwovens which are capable of passing sterilants and retarding ingress of bacteria and other contaminants post sterilization. In other application, the sheet of filter material or media 114 can be a multiple-use item that is capable of reprocessing for additional use(s). Generally, reusable materials can include synthetic woven materials and microporous films (e.g., PTFE films or membranes), which are capable of passing sterilants and retarding ingress of bacteria and other contaminants.

Sterilizable nonwoven filter or media materials present several advantages due to their barrier properties, economics, and consistent quality. The nonwoven materials can be made from a variety of processes including, but not limited to, air laying processes, wet laid processes, hydroentangling processes, spunbonding, meltblowing, staple fiber carding and bonding, and solution spinning. The fibers themselves can be made from a variety of both natural and synthetic materials including, but not limited to, cellulose, rayon, nylon, polyesters, polyolefins, and many other materials. The fibers may be relatively short, staple length fibers, typically less than three inches, or longer and substantially more continuous fibers such as are produced by spunbonding and meltblowing processes. Whatever materials are chosen, the resultant sheet of filter material 114 must be compatible with the particular sterilization technique being used and must also provide both strength and barrier properties to maintain the sterile nature of the contents of the sterilization package system 100 until use. In the illustrated exemplary embodiment, shown in FIGS. 3 and 5, the sheet of filter material 114 can be a transparent breathable film, a translucent or opaque material, such as, e.g., a translucent breathable film, a SMS material (described below), or the like.

For example, the sheet of filter material 114 may be a spunbonded-meltblown-spunbonded material is made from three separate layers that are laminated to one another. The method of making these layers is known and described in U.S. Pat. No. 4,041,203 to Brock, et al., which is incorporated herein in its entirety by reference. The material of Brock, et al. is a three-layer laminate of spunbonded-meltblown-spunbonded layers that is also commonly referred to by the acronym "SMS." The two outer layers of SMS are a spunbonded material made from extruded polyolefin fibers, or filaments, laid down in a random pattern and then bonded to one another. The inner layer is a meltblown layer also made from extruded polyolefin fibers generally of a smaller diameter than the fibers in the spunbonded layers. As a result, the meltblown layer provides increased barrier properties due to its fine fiber structure, which permits the sterilizing agent to pass through the fabric while preventing passage of bacteria and other contaminants. Conversely, the two outer spunbonded layers provide a greater portion of the strength factor in the overall laminate. The laminate may be prepared using an intermittent bond pattern that is preferably employed with the pattern being substantially regularly repeating over the surface of the laminate. The pattern is selected such that the bonds may occupy about 5% to about 50% of the surface area of the laminate. Desirably, the bonds may occupy about 10% to about 30% of the surface area of the laminate. In an exemplary embodiment, the sheet of filter material 114 can be made from a SMS material, but it is to be understood that the sheet of filter material 114 also may be made from other suitable materials.

In one particular embodiment, as shown in FIG. 3, structural support can be provided to the sheet of filter material 114 in the form of a plurality of longitudinal support members 115 extending in a longitudinal direction L and a plurality of transverse support members 116 extending in a transverse direction T disposed on a upper surface 113 of the sheet of filter material 114, although it is to be understood that, alternatively, the longitudinal support members 115 and/or the transverse support members 116 can be disposed on a lower surface (not shown) of the sheet of filter material 114. Such an arrangement can provide the sheet of filter material 114 with improved structural durability. In addition, it is to be understood that the structural support can take any suitable shape or form and is not limited to the longitudinal support members 115 and transverse support members 116 shown in FIG. 3. For instance, the structural support can be in the form of a metal mesh or grid that is incorporated into the sheet of filter material 114 itself.

In still another embodiment and referring to FIG. 4, the filter component of the sealing assembly 108 can be a corrugated sheet of filter material 117. As shown, the corrugated sheet of filter material 117 includes a plurality of peaks 118 and valleys 119, where such a geometry can increase filtration efficiency and provide increased structural robustness to the filter component of the sealing assembly 108.

Referring now to FIG. 5, various features of the gasket 110 of the sealing assembly 108 are shown. Specifically, the gasket 110 completely surrounds the sheet of filter material 114 and provides a continuous sealing interface between the lid 102 and base 104 of the sterilization packaging system 100. The system 100 includes a gasket 110 that may be generally smooth and may have alternating indentations 157 and protrusions 156 on its upper surface 150 to facilitate the delivery of sterilization agent 122 (e.g., steam, ethylene oxide, hydrogen peroxide plasma/vaporized hydrogen peroxide, etc.) into the base 104 of the sterilization packaging system via the sheet of filter material 114 to sterilize the contents contained within the volume 190 of the base 104. The lid 102 can include protrusions 160 that align with the indentations 157 of the gasket 110 to create a channel 162 to facilitate the delivery of the sterilization agent 122. The protrusions 156 on the upper surface 150 of the gasket 110 may additionally assist with sealing the gasket 110 with the lip 123 of the lid 102. In addition, as shown in FIG. 5, the gasket 110 can include a pair of interior-facing, opposing tabs 111 and 112. While opposing tabs 111 and 112 are shown attached to the short side of sealing assembly 108, in another embodiment, opposing tabs 111 and 112 may be disposed on the long side, where the tabs extends from one side to other. The tabs 111 and 112 can facilitate aseptic removal of the sealing assembly 108 once the lid 102 is removed to expose the sterilized contents contained within the packaging system 100 in the operating room, cardiac catheterization lab, emergency room, labor and delivery room, intensive care unit, pediatric care unit, specialized burn care units, or any other surgical or medical unit.

Figure 14:
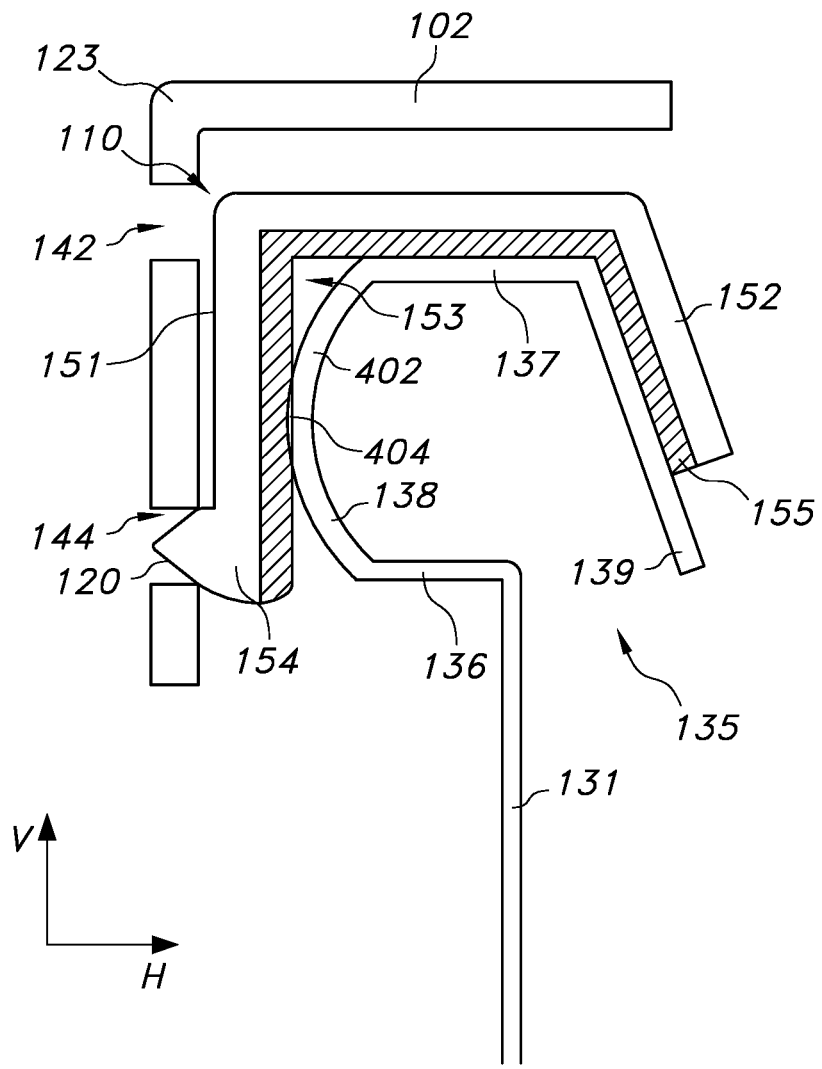
FIG. 14 a partial cross-section view of the sterilization packaging system according to another exemplary embodiment of the present invention.
Figure 15:
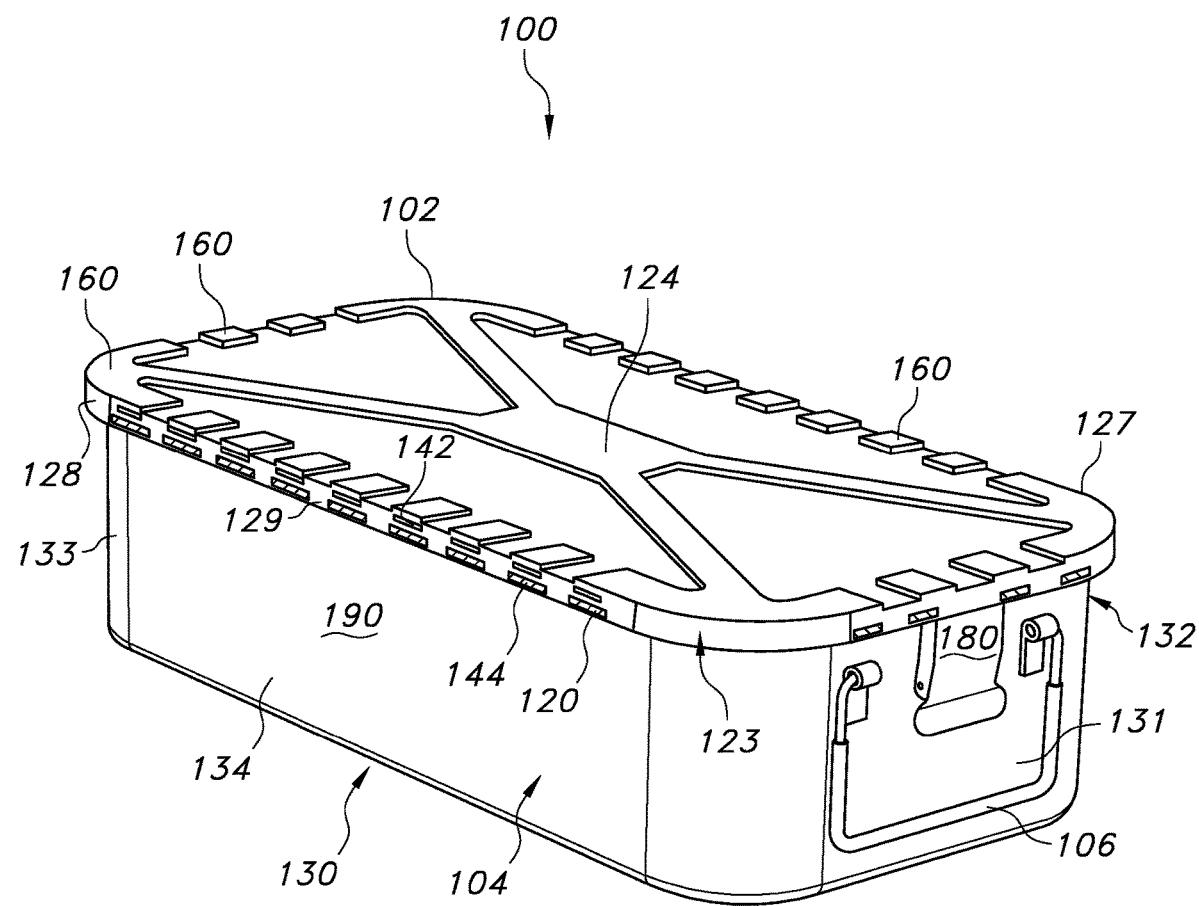
FIG. 15 provides a perspective view of a sealed sterilization packaging system according to another exemplary embodiment of the present invention.

As shown in FIGS. 8-9, the upper surface 150 of the gasket 100 can overlap the perimeter of the sheet of filter material 114. The gasket 100 can encase the perimeter of the sheet of filter material or media 114 as shown in FIGS. 8-9 by bonding or integrating the filter material or media 114 into the inner edge 152 of the gasket 100 to create a secure sealing interface between the gasket 100 and the sheet of filter material or media 114. Further, as illustrated in FIG. 9, the inner edge 152 of gasket 110 can form a first side portion extending downward from the upper surface 150, and the outer edge 151 of gasket 110 can form a second side portion extending from the upper surface 150. As shown in FIGS. 9 and 14, the upper surface 150, first side portion formed by inner edge 152, and second side portion formed by outer edge 151 can define a recess 153 that can receive the base 104 when sealing the lid 102 against the base 104.

Moreover, although the gasket 110 can be formed from a single material, such as polyurethane, silicone, polyvulcanate, polyvinylidene chloride (PVDC), polytetrafluoroethylene (PTFE), polysulphones, a crosslinked elastomers, etc., in some embodiments, the gasket 110 can include a first gasket material 154 and a second gasket material 155, where the first gasket material 154 is more rigid and less compressible than the second gasket material 155. As such, the first gasket material 154 can provide structural support to the sheet of filter material 114, as the sheet of filter material 114 extends from the inner edge 152 of the gasket 110, which is defined by the first gasket material 154 as shown in FIG. 9. For example, the first gasket material 154 can be formed from a rigid polymer such as non-foamed polyurethane, silicone, polyvulcanate, polyvinyl chloride (PVC), polyvinylidene chloride (PVDC), polyvinylidene fluoride (PVDF), polytetrafluorethylene (PTFE), crosslinked and mineral filled elastomers, and other hard durometer materials, while the second gasket material 155 can be formed from a more compressible material such as a foam, including foamed polyurethane, foamed silicones, foamed polyvinyl chloride (PVC), foamed elastomers, foamed polyvinylidene chloride (PVDC), polyvinylidene chloride (PVDF), and other soft durometer polymers, which can be located beneath the upper surface 150 of the gasket 110 and on the sections of the first side portion formed by inner edge 152 of the gasket 110, the second side portion formed by outer edge 151 of the gasket 110 that define the recess 153 so that the gasket 110 is sufficiently compressible to adequately seal the lid 102 to the base 104 at the seal rim 135. In one particular embodiment, the first gasket material 154 and the second gasket material 155 can be formed from the same base material but with different compression properties. For example, the first gasket material 154 and the second gasket material 155 can be the same polymer with two different durometers, where second gasket material 155, which is the material closer to the interface with the seal rim 135, has a lower durometer.

Figure 11:
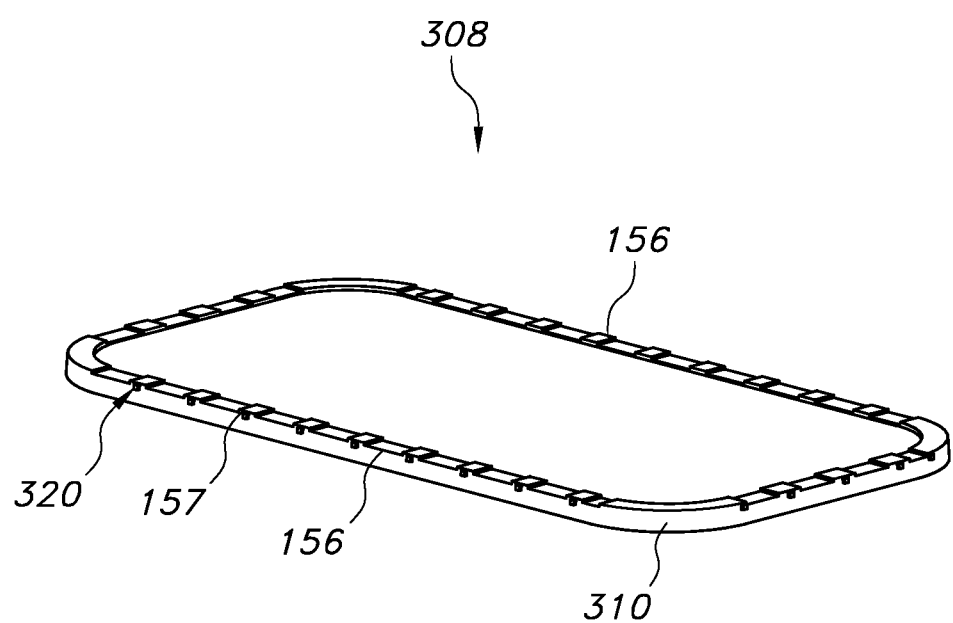
FIG. 11 provides a perspective view of a sealing assembly utilized in the sterilization packaging system of FIG. 10.

In addition, the gasket 110 can include a visual indicator 120 that can be present on the outer edge 151 of the gasket. As the gasket 110 is compressed to create a seal between the lid 102 and the base 104 of the sterilization packaging system 100, such as via the sliding-lock system 200 or latch 180, the visual indicator 120, which can have a different color, texture, or a combination thereof, than the rest of the gasket 110, can be visible from the lower openings 144 in the lip 123 of the lid 102 to signal to a viewer that the sterilization packaging system 100 is sufficiently sealed to protect against the ingress of contaminants. In certain embodiments, such as that shown in FIG. 9, the gasket 110 can be designed such that the visual indicator 120 is aligned horizontally on the outer edge 151 of gasket 110 and can protrude through horizontal lower openings 144 in the lip 123 of the lid 102 when the sterilization packaging system 100 is sufficiently sealed. In such embodiment, the horizontal lower openings 144 for the horizontal visual indicators 120 are generally parallel to the horizontal upper openings 142 for the sterilization agent 122. In an alternative embodiment, as shown in FIGS. 10-11, visual indicators 320 may be vertically aligned on an outer surface 352 of a gasket 310 and the lid 302 may include vertically aligned openings 344 through which the vertical visual indicators 320 can protrude. In the embodiment of FIGS. 10-11, the vertical openings 344 for the visual indicators 320 and the horizontal openings 342 for the sterilization agent 122 are generally alternately disposed around the lip 323 of the lid 302. The horizontally aligned visual indicators 120 (e.g., FIGS. 8-9) and the vertically aligned visual indicators 320 (e.g., FIGS. 10-11) can have a cross-sectional shape configured to protrude through the horizontal lower openings 144 and the vertical openings 344, respectively. For example, the cross-sectional shape of the horizontally aligned visual indicators 120 and the vertically aligned visual indicators 320 can be rectangular, triangular, trapezoidal, or any other suitable profile shape.

Further, although the gasket 110 can be disposable to eliminate the risk of wear and tear on the gasket, which can result in inadequate sealing capabilities, in some embodiments, the gasket 110 can be formed from a reusable material that is more durable, such as elastomeric silicone, polytetrafluoroethylene, polyvinylidene fluoride, polyurethane, a polyolefin (e.g., polyethylene or polypropylene) that can withstand multiple sterilization cycles without losing their compressibility.

Turning now to FIGS. 7 and 9, the seal rim 135 of the base 104 of the sterilization packaging system 100 is discussed in more detail. As mentioned above, the first sidewall 131, the second sidewall 132, the third sidewall 133 and the fourth sidewall 144 of the base 104 terminate at seal rim 135. A cross-sectional view of the seal rim 135 at first sidewall 131 is shown in FIG. 7 for illustrative purposes. The sidewall 131 terminates at a lower horizontal flange 136 of the seal rim 135, which extends away from the opening 109 defined by the base 104 in the horizontal direction H. Further, an outer vertical flange 138 extends from the lower horizontal flange 136 in the vertical direction V, and an upper horizontal flange 137 then extends from the outer vertical flange 138 towards the opening 109 in the base 104. An inner vertical flange 139 then extends downward from the upper horizontal flange 137 in the vertical direction, where the outer vertical flange 136, the upper horizontal flange 137, and the inner vertical flange 139 define a geometry that corresponds with the shape of the recess 153 in the gasket 110, as shown in FIG. 9.

Referring now to FIG. 9, a perspective view of a portion of the sterilization packaging system 100 in its sealed state is described. As shown, the one-piece sealing assembly 108 including the gasket 110 and the sheet of filter material 114 extending from an inner edge 152 therefrom seals the lid 102 to the base 104 when the sliding-lock system 200 or latch 180 is locked into place between the lid 102 and the base 104, resulting in compression of the gasket 110 against and around the seal rim 135. Further, to indicate to a viewer that the sterilization packaging system 100 is adequately sealed, a visual indicator 120 can be visible from and/or can protrude from the lower opening 144 in the lip 123 of the lid 102. Meanwhile, sterilization agent 122 can flow from the environment through the upper opening 142 in the lip, pass over the upper surface 150 of the gasket, and across the gasket 110 to the sheet of filter material 114, where the sterilization agent 122 can then penetrate into the volume 190 of contents to be sterilized located in the base 104. Further, the shape, size, and placement of the protrusions 160 in the lid 102 can be optimized to achieve the correct vent to volume ratio across the various sterilization modalities. In addition, the upper surface 150 of the gasket 110, including the optional protrusions 160, if present, are in contact with the upper surface 124 of the lid 102 as the lid 102 is moved downward and secured to the base 104 by the sliding-lock system 200 or latch 180. In the opposite direction, the upper horizontal flange 137, the outer vertical flange 138, and the inner vertical flange 139 fit into the recess 153 in the gasket 110 as the gasket 110 compresses and forms a seal around the seal rim 135. As a result of such an arrangement, a continuous, one-piece sealing interface is created between the lid 102 and the base 104, which eliminates the need for multiple seal interfaces, while also indicating to the user that a proper seal has been achieved to confirm that the sterilization packaging system 100 is indeed closed.

In addition, as also shown in FIGS. 1 and 8-9, the protrusions 160 present on the upper surface 124 of the lid 102 in conjunction with the upper surface 150 of the gasket 104 define channels 162 to facilitate the delivery of a sterilization agent 122 through the upper openings 142 on the lip 123 of the lid 102 through the channels 162 and ultimately to the sheet of filter material 114 so that the contents of the sterilization packaging system 100 can be sterilized. Further, the protrusions 160 can extend an overhang distance 164 past the inner edge 152 of the gasket 110 to ensure that the sterilization agent 122 can reach the sheet of filter material 114.

Referring now to FIGS. 8-9, partial perspective views of the sterilization packaging system 100 are shown. Specifically, the seal rim 135 contains certain geometry to ensure that the visual indicator 120 can protrude through the lower opening 144 in the lip 123 of the lid 102 when the one-piece sealing assembly 108 is adequately sealed and correctly installed. For instance, an angle θ can be formed between the outer vertical flange 138 that extends in the vertical direction V and the lower horizontal flange 136 that extends in the horizontal direction that is offset slightly from the vertical direction or axis V. For instance, the angle formed between the outer vertical flange 138 and the lower horizontal flange 136 can range from about 65° to about 90°, such as from about 70° to about 85°, such as from about 75° to about 80°. Likewise, the angle α formed between the outer edge 151 of the gasket 110 and the outer vertical flange 138 can range from about 0° to about 25° C., such as from about 5° to about 20°, such as from about 10° to about 15°, where the deflection movement of the gasket 110 including the visual indicator 120 relative to the outer vertical flange 138 facilitates the visual indicator 120 to protrude from the lower opening 144. In this manner, the position of the outer vertical flange 138 encourages the compression of an optional second gasket material 155 and the proper placement of the outer edge 151 of the gasket 110 so that the visual indicator 120 can protrude through the lower openings 144 in the lip 123 of the lid 102, which signals to the user that the gasket 102 is properly sealed between the seal rim 135 and the lid 102.

Referring now to FIG. 14, a partial cross-section view of a sterilization packaging system according to another exemplary embodiment of the present invention is shown. Specifically, the seal rim 135 contains certain geometry to ensure that the visual indicator 120 can protrude through the lower opening 144 in the lip 123 of the lid 102 when the one-piece sealing assembly 108 is adequately sealed and correctly installed. For instance, the outer vertical flange 138 that extends in the vertical direction V can have a curved section 402 where the curved section 402 includes an area of compression 404 formed at a point of tangency with the gasket 110 (e.g., the second gasket material 155), where the deflection movement of the gasket 110 including the indicator 120 relative to the outer vertical flange 138 facilitates the indicator 120 to protrude from the lower opening 144. In this manner, the position of the outer vertical flange 138 encourages the compression of the optional second gasket material 155 and the proper placement of the outer edge 151 of the gasket 110 so that the visual indicator 120 can protrude through the lower openings 144 in the lip 123 of the lid 102, which signals to the user that the gasket 102 is properly sealed between the seal rim 135 and the lid 102. Whereas FIG. 14 is illustrated as having horizontally aligned visual indicators 120, it is to be understood that vertically aligned visual indicators such as those shown in the embodiment of FIGS. 10-11 may be used with a base having a curved outer vertical flange 138 as shown in FIG. 14.

Turning now to FIGS. 10-11, an alternative embodiment of the rigid sterilization container 300 is shown. The rigid sterilization container 300 includes a lid 302 and a gasket 310 that fit onto a base 104 as shown in previous drawings. The lid 302 includes horizontal openings 342 to facilitate the introduction of the sterilization agent and vertical openings 344 which can expose a visual indicator 320 when the lid 302 is adequately and properly sealed to the base 104. The horizontal openings 342 can be aligned with the protrusions 360 on the lid 302. The vertical openings 344 can be interposed between the protrusions 360 and/or the horizontal openings 342 on the lid 302. The gasket 310 can include a visual indicator 320 that is vertically oriented and which can be present on the outer edge 351 of the gasket. By having vertical visual indicators 320 visible through vertical openings 344 adjacent to horizontal openings 342, a user may have an easy and clear way to check the integrity of the seal of the rigid sterilization container 300 without confusing which opening of the openings 342 and 344 is intended to indicate the seal. As the gasket 310 is compressed to create a seal between the lid 302 and the base 104 of the sterilization packaging system 300, such as via the latch 180 or sliding-lock system 200, the visual indicator 320 can be visible from the vertical openings 344 in the lip 323 of the lid 302 to signal to a viewer that the sterilization packaging system 100 is sufficiently sealed to protect against the ingress of contaminants. In some embodiments, the visual indicator 320 can have a different color, texture, or a combination thereof, than the rest of the gasket 310. In certain embodiments, such as that shown in FIGS. 10 and 11, the gasket 310 can be designed such that the visual indicator 320 can protrude through the vertical openings 344 in the lip 323 of the lid 302 when the sterilization packaging system 300 is sufficiently sealed. The downward force of pressing the lid 302 on the gasket 310 may effectively transfer towards pushing the vertical visual indicators 320 out through the lid 302. The amount of downward force to push the visual indicators 320 out through openings 344 in the lid 302 can be reduced compared to the amount of downward force necessary to push visual indicators 120 out through openings 144 in the lid 102 because the force is transferred more effectively. As such, this embodiment has improved ergonomics for the user because less downward force is required in order to effectively seal and lock the lid 302 onto the base 104.

Referring again to FIGS. 1-2, an embodiment of a sliding-lock system 200 in place of the vertical latch 180 is illustrated. The sliding-lock system 200 includes a slide-lock handle 202 provided on the lid 102. In one embodiment, the slide-lock handle 202 can be formed from a material having a color that contrasts a color of the base 104 and/or a color of the lid 102. The slide-lock handle 202 is provided with a plurality of locking fingers 204, 206, 208. The seal rim 135 of the base 104 is provided with a corresponding plurality of locking fingers 214, 216, 218. The three handle locking fingers 204, 206, 208 and the three base locking fingers 214, 216, 218 come together to form a lock having three points of locking (see e.g. FIGS. 12C and 13A-C). However, it is to be understood that the number of locking fingers shown in FIGS. 2, 12A-C and 13A-C are exemplary and the quantity of locking fingers, and thereby points of locking, may vary. For example, the sliding-lock system 200 may include two pairs of locking fingers, or four pairs of locking fingers, or five pairs of locking fingers, etc. The base 104 additionally includes a slide mount 232 positioned above the locking fingers 214, 216, 218. The slide mount 232 provides a horizontal guide for sliding the slide-lock handle 202 into the locked position on the base 104. The slide mount 232 additionally may include an angled cutting surface 234. The slide-lock handle 202 additionally may include an aperture 230 which is specially shaped for allowing the use of a tamper-proof tag 240, and at least one recess 252 which is configured to receive a means for providing tactile feedback.

FIGS. 12A-D and 13A-D illustrate the use of the sliding-lock system 200. As shown in FIG. 12A, the lid 102 is pushed down onto the base 104, compressing the gasket 110, and the slide-lock handle 202 on the lid 102 can be positioned such that the handle locking fingers 204, 206, 208 and the base locking fingers 214, 216, 218 are generally alternately aligned. The slide-lock handle 202 can be moved in a vertical direction downward from the lid 102 to engage with the base locking fingers 214, 216, 218. Then, as shown in FIGS. 12B and 12C, the handle 202 slides horizontally along the slide mount 232 to tighten the seal, further compressing the gasket 110, thereby closing and locking the lid 102 onto the base 104. As illustrated in FIGS. 12D and 13D, the slide-lock handle 202 may slide in only one horizontal direction to seal the container. When the handle 202 is slid in the locking direction, the locking fingers 204, 206, 206 of the slide-lock handle 202 slide beneath the locking fingers 214, 216, 218 of the base such that the locking fingers become vertically aligned, as shown in FIG. 12C. The vertical alignment of the locking fingers 202, 204, 206, 214, 216, 218 maintains compression of the gasket 110 and keeps the container closed. Additionally, the handle 202 can include at least one ball plunger 250 (shown in FIG. 12E) to provide tactile feedback of closing the lid 102 on the base 104 and sliding the handle 202 to seal the lid 102 onto the base 104. The ball plunger 250 can be made of a stem 254 and a ball nose 256. The stem 254 of each ball plunger 250 can fit within a recess 252 on the bottom side 202a (see FIG. 2) of the slide-lock handle 202 such that the ball nose 256 extends from the slide-lock handle 202. When the slide-lock handle 202 is moved vertically downward to engage the base 104, the ball nose can be pushed against the base 104 by a nose force 258 to depress the ball nose 256 into the stem 254. The nose force 258 required to overcome the resistance by the ball nose 256 and the friction generated from sliding the depressed ball nose 256 against the base 104 can thereby provide tactile feedback to a user sliding the handle 202 to lock the handle 202 onto the base 104. For example, the handle 202 can include two recesses 252 in order to receive two ball plungers 250 for providing tactile feedback (see FIGS. 2, 12A-C and 12E). Further, there can be a mechanism, e.g. a pin, that can provide an audible sound when the slide-lock handle 202 is locked onto the base 104. Further, the handle 202 can include a ball plunger which provides tactile feedback of closing the lid 102 on the base 104 and sliding the handle 202 to seal the lid 102 onto the base 104.

As mentioned above and illustrated in FIGS. 13A-D, the sliding-lock system 200 may further include a tamper-proof tag 240. The tamper-proof tag 240 may be inserted through the specially formed aperture 230 in the slide-lock handle 202 only when the slide-lock handle 202 is fully closed, as shown in FIG. 13A. Prior to horizontally sliding and locking the slide-lock handle 202, the aperture 230 is blocked by the slide mount 232 (see, e.g., FIGS. 12A-B). The tamper-proof tag 240 can include one or a plurality of protrusions 242 and an indented region 244. The protrusions 242 can be located at the bottom of the tamper-proof tag 240 and can rest against the slide-lock handle 202 to hold the tamper-proof tag 240 in place after insertion. The protrusions 242 can also optionally make an audible sound when the tamper-proof tag 240 has been properly inserted through the aperture 230. The indented region 244 of the tamper-proof tag 240 can be aligned with the cutting surface 234 of the slide mount 232. Once the tamper-proof tag 240 has been inserted in the aperture 230, when the slide-lock handle 202 is slid in the horizontal direction opposite the locking direction, the cutting surface 234 of the slide mount 232 cuts the tamper-proof tag 240 at the indented region 244, as shown in FIG. 13C. The tamper-proof tag 240 being cut by the cutting surface 234 functions as a tamper-evident mechanism so that an observer can determine if the sterilization container 100 has been opened and the seal been broken.

The slide-lock handle 202, including the locking fingers, may be manufactured from suitable durable strength materials, such as metals, ceramics, polymers, or composite alloys. Examples of metals can include stainless steel, titanium, or aluminum. Examples of polymers can include nylon, polyphenylsulfone (PPSU) or polyetheretherketone (PEEK). The slide-lock may additionally include an integrated graphic that indicates the locking direction. The sliding-lock system 200 may further include a color option on the slide-lock handle 202 of the lid 102. The color option on the slide-lock handle 202 may be, for example, pigments if the slide-lock handle 202 is made of a polymer, or screen printing or anodized if the slide-lock handle 202 is made of aluminum, or other forms of coloring of the slide-lock handle 202.

Further, it is to be understood that although not repeated in detail with respect to FIGS. 10-11, any of the various features described above with respect to FIGS. 1-9 and 12A-16 and sterilization packaging system 100 may also be incorporated into the sterilization packaging system 300 to the extent that such features do not conflict with the features required by sterilization packaging system 300.

This written description uses examples to disclose the invention, including the best mode, and also to enable any person skilled in the art to practice the invention, including making and using any devices or systems and performing any incorporated methods. The patentable scope of the invention is defined by the claims and may include other examples that occur to those skilled in the art. Such other examples are intended to be within the scope of the claims if they include structural elements that do not differ from the literal language of the claims or if they include equivalent structural elements with insubstantial differences from the literal language of the claims.

What is claimed is:

1. A sealing assembly for a sterilization packaging system, the sealing assembly comprising:
   a gasket having an upper surface extending from an outer edge to an inner edge, wherein the upper surface comprises indentations extending from the outer edge to the inner edge, wherein each indentation defines a channel to facilitate delivery of a sterilization agent; and
   a sheet of filter material extending from an inner edge of the gasket, wherein the gasket completely surrounds and partially overlaps the sheet of filter material, wherein the gasket facilitates the delivery of the sterilization agent through the sheet of filter material when the sterilization packaging system is sealed with the sealing assembly.

2. The sealing assembly of claim 1, wherein the gasket comprises a first gasket material and a second gasket material, wherein the first gasket material is less compressible and more rigid than the second gasket material, further wherein the inner edge is defined by the first gasket material.

3. The sealing assembly of claim 2, wherein at least one visual indicator is present on an outer edge of the gasket, wherein the outer edge of the gasket is defined by the first gasket material.

4. The sealing assembly of claim 3, wherein a long side of each visual indicator extends in a vertical direction.

5. The sealing assembly of claim 3, wherein a long side of each visual indicator extends in a direction perpendicular to an upper surface of the sheet of filter material.

6. The sealing assembly of claim 1, wherein the sheet of filter material extends in a longitudinal direction and a transverse direction, wherein one or more longitudinal support members is disposed on a surface of the sheet of filter material in the longitudinal direction and one or more transverse support members is disposed on the surface of the sheet of filter material in the transverse direction.

7. The sealing assembly of claim 1, wherein the sealing assembly provides a continuous sealing interface between a lid and a base of the sterilization packaging system.

8. The sealing assembly of claim 1, wherein the gasket includes a pair of interior facing opposing tabs.

9. A sterilization packaging system having a volume for containing items to be sterilized, the sterilization packaging system comprising:
a lid having an upper surface defining a perimeter and a lip extending downward from the perimeter, wherein the upper surface comprises a plurality of protrusions, and wherein the lip includes a plurality of openings;
a base having a lower surface, a first sidewall, a second sidewall, a third sidewall, and a fourth sidewall extending from the lower surface, wherein the first sidewall, the second sidewall, the third sidewall, and the fourth sidewall terminate at a seal rim defining a perimeter;
a sealing assembly, wherein the sealing assembly seals the lid to the seal rim of the base, the sealing assembly comprising:
a gasket having an upper surface, an outer edge, and an inner edge, wherein the upper surface of the gasket and each of the plurality of protrusions on the upper surface of the lid define a respective channel therebetween,
a sheet of filter material extending from the inner edge of the gasket, wherein the gasket completely surrounds and partially overlaps the sheet of filter material, wherein each channel defined by each of the plurality of protrusions and the upper surface of the gasket facilitates the delivery of sterilization agent through the sheet of filter material when the sterilization packaging system is sealed with the sealing assembly; and
a sliding-lock mechanism to close and lock the lid to the base, the sliding-lock mechanism comprising a slide-lock handle on the lid, wherein the slide-lock handle comprises a plurality of locking fingers, and wherein the base further includes a plurality of corresponding locking fingers.

10. The sterilization packaging system of claim 9, wherein at least one visual indicator is present on the outer edge of the gasket.

11. The sterilization packaging system of claim 10, wherein the visual indicator is visible from an opening in the lip when the sterilization packaging system is adequately sealed by the sealing assembly.

12. The sterilization packaging system of claim 10, wherein the visual indicator protrudes from an opening in the lip when the sterilization packaging system is adequately sealed by the sealing assembly.

13. The sterilization packaging system of claim 10, wherein the plurality of openings on the lip of the lid comprise horizontal openings, vertical openings, or a combination thereof.

14. The sterilization packaging system of claim 13, wherein horizontal openings align with each of the plurality of protrusions to facilitate delivery of the sterilization agent through the sheet of filter material via the channels when the sterilization packaging system is sealed with the sealing assembly.

15. The sterilization packaging system of claim 13, wherein the plurality of openings comprises the horizontal openings and the vertical openings that are alternately disposed around the lip of the lid.

16. The sterilization packaging system of claim 13, wherein the at least one visual indicator is visible from at least one respective vertical opening when the sterilization packaging system is adequately sealed by the sealing assembly.

17. The sterilization packaging system of claim 13, wherein the at least one visual indicator protrudes from at least one respective vertical opening when the sterilization packaging system is adequately sealed by the sealing assembly.

18. The sterilization packaging system of claim 10, wherein the openings on the lip of the lid comprise upper openings and lower openings.

19. The sterilization packaging system of claim 18, wherein the upper openings align with each of the plurality of protrusions to facilitate delivery of the sterilization agent through the sheet of filter material via the channels when the sterilization packaging system is sealed with the sealing assembly.

20. The sterilization packaging system of claim 18, wherein the at least one visual indicator is visible from a respective one of the lower openings when the sterilization packaging system is adequately sealed by the sealing assembly.

21. The sterilization packaging system of claim 18, wherein the at least one visual indicator protrudes from a respective one of the lower openings when the sterilization packaging system is adequately sealed by the sealing assembly.

22. The sterilization packaging system of claim 9, wherein the sealing assembly provides a continuous sealing interface between the lid and the base of the sterilization packaging system.

23. The sterilization packaging system of claim 9, wherein the plurality of protrusions extend an overhang distance past an inner edge of the upper surface of the gasket to ensure the sterilization agent can reach the sheet of filter material.

24. The sterilization packaging system of claim 9, wherein the upper surface of the gasket comprises a plurality of indentations and protrusions, wherein each of the plurality of indentations aligns with the protrusions on the lid to define each respective channel.

25. A sliding-lock system for closing and locking together a base and a lid of a container, the base having a lower surface, a first sidewall, a second sidewall, a third sidewall, and a fourth sidewall extending from the lower surface, wherein the first sidewall, the second sidewall, the third sidewall, and the fourth sidewall terminate at a seal rim defining a perimeter, the lid having an upper surface defining a perimeter corresponding to the perimeter of the base and a lip extending downward from the perimeter, the sliding-lock system comprising:

a plurality of locking fingers protruding from the seal rim of at least one sidewall of the base;

a slide mount positioned above the plurality of locking fingers on the base; and at least one handle comprising an aperture for inserting a tamper-proof tag when the lid is locked in place on the base, wherein each handle is positioned on the lip of the lid, further wherein each handle has a plurality of locking fingers corresponding to the locking fingers of the base;

wherein when the lid is pushed down on the base, the locking fingers of the base engage the locking corresponding fingers of the lid, such that the handle slides horizontally in a locking direction guided by the slide mount to tighten and lock the lid in place on the base.

26. The sliding-lock system of claim 25, wherein the sliding-lock system further includes a tamper proof tag inserted through the aperture, further wherein the tamper-proof tag may be cut by a cutting edge of the slide mount when the handle is slid in a direction opposite the locking direction.

27. The sliding-lock system of claim 25, wherein the locking fingers of the base are disposed vertically above the corresponding locking fingers of the lid when the lid is locked in place on the base.

28. The sliding-lock system of claim 25, wherein the plurality of locking fingers of the base each comprises a rectangular cross-sectional shape.

29. The sliding-lock system of claim 25, wherein each of the plurality of locking fingers of the at least one handle comprises opposing angled sliding side surfaces for sliding along the locking fingers of the base.

30. The sliding-lock system of claim 25, wherein each of the plurality of locking fingers of the at least one handle comprises a trapezoidal cross-sectional shape.

* * * * *